United States Patent
Boehler et al.

(10) Patent No.: US 12,186,027 B2
(45) Date of Patent: Jan. 7, 2025

(54) MEDICAL BENDING SYSTEM

(71) Applicant: Aesculap AG, Tuttlingen (DE)

(72) Inventors: Lukas Boehler, Furtwangen (DE); Josef Kozak, Tuttlingen (DE); Mateusz Daniol, Kozlow (DE); Andreas Alk, Spaichingen (DE)

(73) Assignee: Aesculap AG, Tuttlingen (DE)

( * ) Notice: Subject to any disclaimer, the term of this patent is extended or adjusted under 35 U.S.C. 154(b) by 529 days.

(21) Appl. No.: 17/512,107

(22) Filed: Oct. 27, 2021

(65) Prior Publication Data

US 2022/0047336 A1 Feb. 17, 2022

Related U.S. Application Data

(63) Continuation of application No. PCT/EP2020/061675, filed on Apr. 28, 2020.

(30) Foreign Application Priority Data

Apr. 30, 2019 (DE) ............... 10 2019 111 177.3

(51) Int. Cl.
*B21D 7/12* (2006.01)
*A61B 34/20* (2016.01)
(Continued)

(52) U.S. Cl.
CPC ............. *A61B 34/20* (2016.02); *A61B 90/08* (2016.02); *A61B 90/39* (2016.02); *B21D 7/12* (2013.01);
(Continued)

(58) Field of Classification Search
CPC ............. B21D 7/14; B21D 7/12; B21D 7/063
See application file for complete search history.

(56) References Cited

U.S. PATENT DOCUMENTS

| | | |
|---|---|---|
| 5,490,409 A | 2/1996 | Weber |
| 9,585,700 B2 | 3/2017 | Wehrle et al. |

(Continued)

FOREIGN PATENT DOCUMENTS

| | | |
|---|---|---|
| DE | 10045375 C2 | 4/2002 |
| DE | 102016115605 A1 | 3/2018 |

(Continued)

OTHER PUBLICATIONS

Written Opinion received in International Application No. PCT/EP2020/061675 dated Aug. 12, 2020, with translation, 11 pages.

(Continued)

*Primary Examiner* — Teresa M Ekiert
(74) *Attorney, Agent, or Firm* — Christopher A. Rothe; CM Law (57) ABSTRACT

A medical bending system for bending an object to be bent, in particular a rod, includes at least one object to be bent, a bending apparatus with which the object to be bent is bendable, and a navigation device having a detection unit and a data processing unit. The object to be bent and the bending apparatus include markings that are optically detectable by the detection unit and are arranged or formed on respective surfaces of the object to be bent and the bending apparatus. The data processing unit determines at least one bending parameter during the bending operation based on information from the detection unit relating to the detected markings.

21 Claims, 4 Drawing Sheets

(51) Int. Cl.
*A61B 90/00* (2016.01)
*B21D 7/14* (2006.01)
(52) U.S. Cl.
CPC ........ *B21D 7/14* (2013.01); *A61B 2034/2055* (2016.02); *A61B 2034/2068* (2016.02); *A61B 2090/3937* (2016.02)

(56) References Cited

U.S. PATENT DOCUMENTS

| | | | |
|---|---|---|---|
| 10,478,882 B1 * | 11/2019 | Perez | B21D 7/14 |
| 10,786,287 B2 | 9/2020 | Beger et al. | |
| 10,905,489 B2 | 2/2021 | Kozak et al. | |
| 10,980,578 B2 | 4/2021 | Beger et al. | |
| 11,440,070 B1 * | 9/2022 | Bergeson | B21D 7/14 |
| 2005/0262911 A1 | 12/2005 | Dankowicz et al. | |
| 2007/0227216 A1 | 10/2007 | Schalliol | |
| 2012/0047980 A1 | 3/2012 | Harper | |
| 2015/0135787 A1 * | 5/2015 | Dani | G01B 5/213 72/31.1 |
| 2018/0055546 A1 | 3/2018 | Beger et al. | |
| 2019/0000372 A1 | 1/2019 | Gullotti et al. | |

FOREIGN PATENT DOCUMENTS

| | | |
|---|---|---|
| EP | 2910206 A1 | 8/2015 |
| EP | 3287093 A1 | 2/2018 |
| EP | 3459478 A1 | 3/2019 |
| WO | 2012062464 A1 | 5/2012 |
| WO | 2016088130 A1 | 6/2016 |
| WO | 2016134911 A1 | 9/2016 |

OTHER PUBLICATIONS

Search Report received in International Application No. PCT/EP2020/061675 dated Aug. 12, 2020, with translation, 5 pages.

* cited by examiner

MEDICAL BENDING SYSTEM

CROSS-REFERENCE TO RELATED APPLICATIONS

This application is a continuation patent application of international application number PCT/EP2020/061675, filed Apr. 28, 2020, and claims the benefit of German application number 10 2019 111 177.3, filed Apr. 30, 2019. The content of international application number PCT/EP2020/061675 and German application number 10 2019 111 177.3 are incorporated herein by reference in their entireties and for all purposes.

FIELD

The present disclosure relates to a medical bending system for bending an object to be bent, in particular a rod, comprising at least one object to be bent, a bending apparatus with which the object to be bent is bendable, and a navigation device with a detection unit and a data processing unit.

BACKGROUND

A bending system of that kind is used, e.g., to bend an object to be bent, in the form of a surgical rod, and to bring it from an initial shape into a predetermined desired shape. For example, the rod is provided for connecting connecting elements, in particular surgical anchoring elements like, for example, pedicle screws. The rod and the pedicle screws are, e.g., constituent parts of a surgical fixation system for fixing vertebrae relative to one another.

For example, the rod must be bent in such a way that it is adapted to the three-dimensional arrangement of the anchoring elements with a view to an optimal implantation result. Here, it is known to optically monitor the actual shape of the rod or to use a template. It is also known to adapt calculated values for the desired shape of the rod with a manual or an automatic bending tool.

Embodiments of bending apparatuses are known, e.g., in US 2012/0047980 A1, U.S. Pat. No. 5,490,409, EP 3 287 093 A1, DE 100 45 375 A1, US 2007/0227216 A1, US 2005/0262911 A1, WO 2016/088130 A1, EP 3 261 564 A1, and EP 2 910 206 A1. In the last-mentioned document, a system and a method are described with which the positions of the anchoring elements relative to one another and/or relative to a rod can be determined in order to ensure a best possible adaptation of the rod to the relative positions of the anchoring elements.

An object underlying the present disclosure is to provide a bending system of the kind stated at the outset, which is handleable in a more user-friendly manner with a simpler construction.

SUMMARY

In an aspect of the disclosure, a medical bending system for bending an object to be bent, in particular a rod, comprises at least one object to be bent, a bending apparatus with which the object to be bent is bendable, and a navigation device with a detection unit and a data processing unit. The object to be bent and the bending apparatus comprise markings that are arranged or formed on the respective surfaces thereof and are optically detectable by the detection unit, wherein the data processing unit is configured to determine at least one bending parameter during the bending operation on the basis of information from the detection unit relating to the detected markings.

BRIEF DESCRIPTION OF THE DRAWINGS

The foregoing summary and the following description may be better understood in conjunction with the drawing figures, of which.

DETAILED DESCRIPTION

Although the disclosure is illustrated and described herein with reference to specific embodiments, the disclosure is not intended to be limited to the details shown. Rather, various modifications may be made in the details within the scope and range of equivalents of the claims and without departing from the disclosure.

The present disclosure related to a medical bending system for bending an object to be bent, in particular a rod. The medical bending system comprises at least one object to be bent, a bending apparatus with which the object to be bent is bendable, and a navigation device with a detection unit and a data processing unit. The object to be bent and the bending apparatus comprise markings that are arranged or formed on the respective surfaces thereof and are optically detectable by the detection unit. The data processing unit is configured to determine at least one bending parameter during the bending operation on the basis of information from the detection unit relating to the detected markings.

The bending system in accordance with the disclosure, unlike conventional bending systems, has the advantage that both the object to be bent, in particular the rod, as well as the bending apparatus itself have at least one respective marking. By contrast, in conventional bending systems, surgical marking devices in the form of so-called "rigid bodies" are used, which are arranged on the bending apparatus and, e.g., on a tool for the object to be bent. While apparatuses of that kind have proven their worth in practice, these marking devices require additional costs and take up space, which makes the handling more difficult for a user. Unlike different conventional automatic bending systems that are difficult to use in a mobile and sterile manner in an operating room, the, in particular handleable, bending system in accordance with the disclosure has improved handling.

In accordance with the disclosure, provision is made that the object to be bent and the bending apparatus itself comprise at least one marking. This makes it possible to detect the markings time-dependently by means of the detection unit, such that both the object to be bent and the bending apparatus itself can be tracked by the navigation device. This makes it possible, in particular, to detect the actual shape of the object to be bent by means of the navigation device during the bending operation and to provide indications relating thereto to the user in order to make it easier for said user to bend the object to be bent into the necessary desired shape.

It is favorable if the markings are integrated into or formed on the surface of the object to bent and/or of the bending apparatus. Here, the markings are advantageously flat, for example two-dimensional structures that do not project or project only slightly over the surface of the bending apparatus and/or of the object to be bent.

The markings are introduced into the surfaces, e.g., by anodic oxidation, a shape-changing exposure method, for example ablatively by means of an ultra-short pulse laser, or by water print coating. Advantageously, a method that does not damage the material of the bending apparatus and/or the object to be bent is used for the introduction or formation of the markings. The markings preferably do not influence the sterile properties of the bending apparatus and/or of the object to be bent.

The use of disposable elements for the markings may be advantageous, alternatively or in addition to direct markings of the object to be bent and/or the bending apparatus.

In a preferred embodiment, provision may be made that the markings are formed separate from and connected to the object to be bent and/or the bending apparatus. This may be advantageous, e.g., in the case of a possible alteration of already existing markings, the detection of which by the navigation device is difficult. The separate markings may be applied, for example, by force-locking engagement, positive engagement, and/or by substance-to-substance bond, for example by means of screw or click connection.

Flatly and, in particular, two-dimensionally extended markings are favorably used.

The markings are preferably designed such that they do not impair the structure and, in particular, the stability and/or the properties of the object to be bent and/or of the bending apparatus for sterilizability.

The navigation device advantageously is or comprises an integrated navigation device, which comprises the detection unit, the data processing unit, and an indication unit. "Integrated" is presently to be understood, in particular, to the effect that the aforementioned units are arranged in a common housing or on a common support device of the navigation device. The indication unit is advantageously of optical and/or acoustic and/or haptic configuration and comprises, in particular, a controllable display unit with an image display and/or a speaker.

The navigation device is or comprises, e.g., a smartphone, a tablet computer, or a head mounted device (HMD), for example in the form of data glasses. In the case of the HMD, indications, for example, are displayed in the field of view of the user.

It is understood that "indications" presently may be instructions to the user or may comprise instructions.

It is advantageous if a desired shape of the object to be bent is determinable by the data processing device on the basis of data from a sensor unit of the navigation device in order to be able to connect together a plurality of connecting elements, arranged in a defined relative arrangement, by way of the object to be bent. For example, a method as is described in EP 2 910 206 A1 is used for the determination of the relative positions of the connecting elements, in particular anchoring elements and special pedicle screws. The positions of the connecting elements can, for example, be graphically displayed to the user on the aforementioned display unit.

Provision may be made that a user himself determines the necessary desired shape, wherein necessary bending parameters may optionally be calculated by the data processing unit.

Alternatively or in addition, the calculation of required bending parameters can advantageously be determined by the data processing unit without intervention by the user. The material of the object to be bent may preferably be considered for determining the bending parameters.

It is advantageous if a predeterminable desired shape of the object to be bent is stored in a storage unit of the navigation device, in particular determined in one of the previously described manners, and if indications to the user regarding at least one of the following are outputted on an indication unit of the navigation device:

information for operating the bending apparatus, wherein values of the at least one bending parameter are determined and on the basis thereof the actual shape of the object to be bent is determined and is compared with the desired shape, wherein preferably indications are provided when the value of the at least one bending parameter has a desired value or differs therefrom. The user can be informed by way of the indication unit whether the value of the at least one bending parameter corresponds to the required value so that the object to be bent can be converted into the desired shape.

indications relating to the selection of an object to be bent from a set of available objects to be bent. For example, the best suited object to be bent can be suggested to the user on the indication unit.

The markings are favorably detected by the detection unit during the bending operation, the bending apparatus and the object to be bent then being able to be tracked during the bending operation. This makes it possible to continuously determine the actual shape of the object to be bent and favorably to continuously monitor the actual shape in order to instruct the user in operating the bending system as to how the object to be bent obtains the desired shape.

Here, indications to the user relating to the actual shape of the object to be bent, in particular the actual value of the at least one bending parameter and the desired value of at least one bending parameter, are advantageously provided by the data processing unit.

The data processing unit is advantageously configured to instruct the user regarding a defined plan of procedure (workflow or the like) for bending the object to be bent. For example, the data processing unit presents the user with indications on the indication unit as to which bending parameter—specifically bending position, bending radius, and bending angle as well as bending plane if necessary—should be implemented next in order to bring the object to be bent into the desired shape.

Provision may be made that the object to be bent, in particular the rod, comprises markings in the form of peripheral rings, which are arranged on the object to be bent at a distance from one another in a longitudinal direction of the object to be bent. The markings are, e.g., spaced at a distance from one another along a longitudinal direction, in particular an axis, of the object to be bent and extend at least over a partial circumference in relation to the axis. Favorably at least one marking is designed such as to be able to determine the orientation of the object to be bent in relation to the axis.

It is favorable if the bending apparatus comprises markings in the form of at least one of the following:

flatly extended markings on surfaces of branches of the bending apparatus, in particular for monitoring a bending angle as a bending parameter;

at least one marking on a rotation receptacle with which the object to be bent is held on the bending apparatus so as to be rotatable about an axis, in particular for monitoring a bending plane as a bending parameter;

at least one marking on an abutment element for placing the object to be bent during the bending operation, in particular for monitoring at least one bending position and/or at least one bending radius as a bending parameter.

The data processing unit favorably uses at least one marking of the bending apparatus for defining a reference coordinate system in space in which the position of the object to be bent relative to the bending apparatus is determinable. Establishing separate coordinate systems for tracking the object to be bent relative to the bending apparatus is thus not necessary.

The data processing unit favorably determines at least one of the following on the basis of detected markings on the object to be bent and on the bending apparatus:

the relative position of the object to be bent and the bending apparatus, for example as described above;

the position of the object to be bent on at least one abutment element of the bending apparatus with regard to the bending position as a bending parameter. For example, a respective marking of the bending apparatus and the object to be bent are used to determine the bending position—by the object to be bent abutting against the abutment element—on the object to be bent.

The data processing unit advantageously determines the orientation of the object to be bent relative to the bending apparatus on the basis of a marking of a rotation receptacle of the bending apparatus with regard to the bending plane as a bending parameter. For example, an eye-shaped rotation receptacle is provided, through which the object to be bent, in particular the rod, is passed. The rotation receptacle can be rotated about an axis defined by same for rotating the object to be bent. The bending plane can be varied in this way.

It is favorable if the data processing unit determines the actual shape of the object to be bent on the basis of markings of the object to be bent. For example, the aforementioned peripheral rings are detected by the navigation device and the actual shape is calculated on the basis of information relating thereto. The actual shape may advantageously be determined for comparison with the desired shape. An indication can favorably be provided to the user on the indication unit regarding the extent to which the actual shape deviates from the desired shape.

The bending apparatus advantageously comprises abutment elements for the object to be bent, which are positioned at a distance from one another and are pivotable relative to one another, wherein the abutment elements are arranged or formed on pivot elements that are pivotable in relation to one another, wherein the data processing unit advantageously determines the bending angle as a bending parameter on the basis of markings on the pivot elements.

The pivot elements are favorably branches that are pivotably mounted on one another. Provision is hereby favorably made that the bending apparatus is hand-operable. For example, the user can grasp the branches with his hand and pivot same relative to one another, the abutment elements thereby acting upon the object to be bent with a bending force. On the basis of the markings, the bending angle can be calculated and, in particular, monitored as a bending parameter by the data processing unit until a desired bending angle is reached.

In a preferred embodiment, the bending apparatus may comprise a delimiting element with which a range of the pivoting of the pivot elements relative to one another is delimitable, wherein an indication to the user for setting the delimiting element is providable on an indication unit with a view to achieving a predetermined bending angle when the pivot elements are pivoted until the delimiting element comes into effect. The delimiting element cooperates with the pivot elements. Said pivot elements can be pivoted relative to one another until the delimiting element comes into effect. When this is the case, the object to be bent has been bent by the desired bending angle.

The bending apparatus may preferably comprise an abutment element for the object to be bent, said abutment element comprising two abutment members that can be brought into different distances from another, different bending radii being achievable depending on the distance of the abutment members from one another. The abutment members may be displaceable relative to one another. Provision may be made that the abutment members are moveable and, in particular, displaceable together with a fixed distance from one another, for example transversely and, in particular, perpendicularly to the direction of the aforementioned displacement. The bending radius can be influenced in this way. Provision may be made that the distance of the abutment members from one another and/or the position is determinable by way of the markings during the joint movement and, in particular, displacement.

The bending apparatus may advantageously have display elements, in particular in the form of scales, on the basis of which the value of at least one bending parameter is readable for the user. In this way, it is possible for the user to use the bending apparatus in a handling-friendly manner, even without a navigation device.

Figure 1:
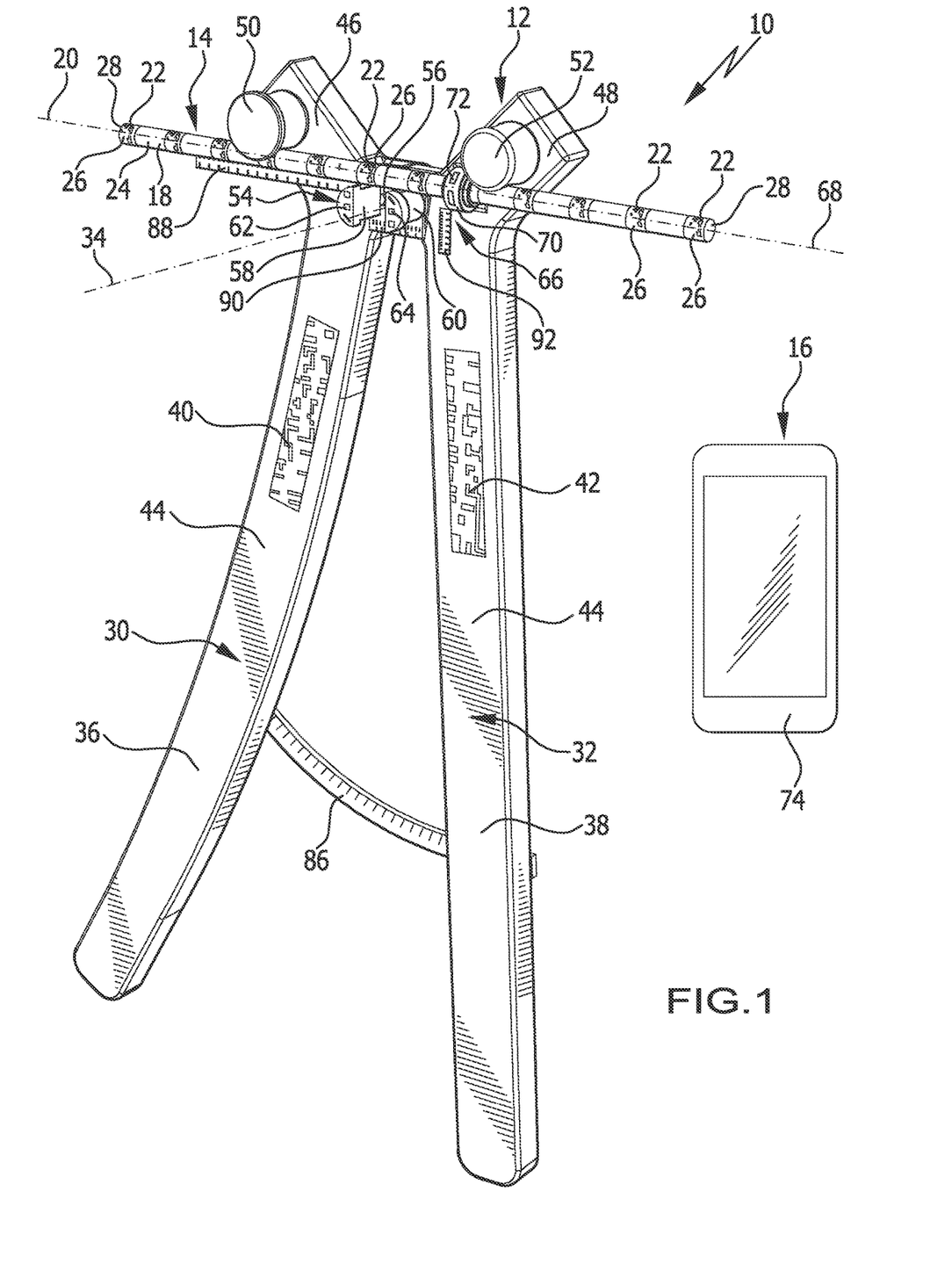
FIG. 1 shows a perspective depiction of a bending system in accordance with the disclosure with a bending apparatus, an object to be bent, and a navigation device that is schematically depicted.
Figure 2:
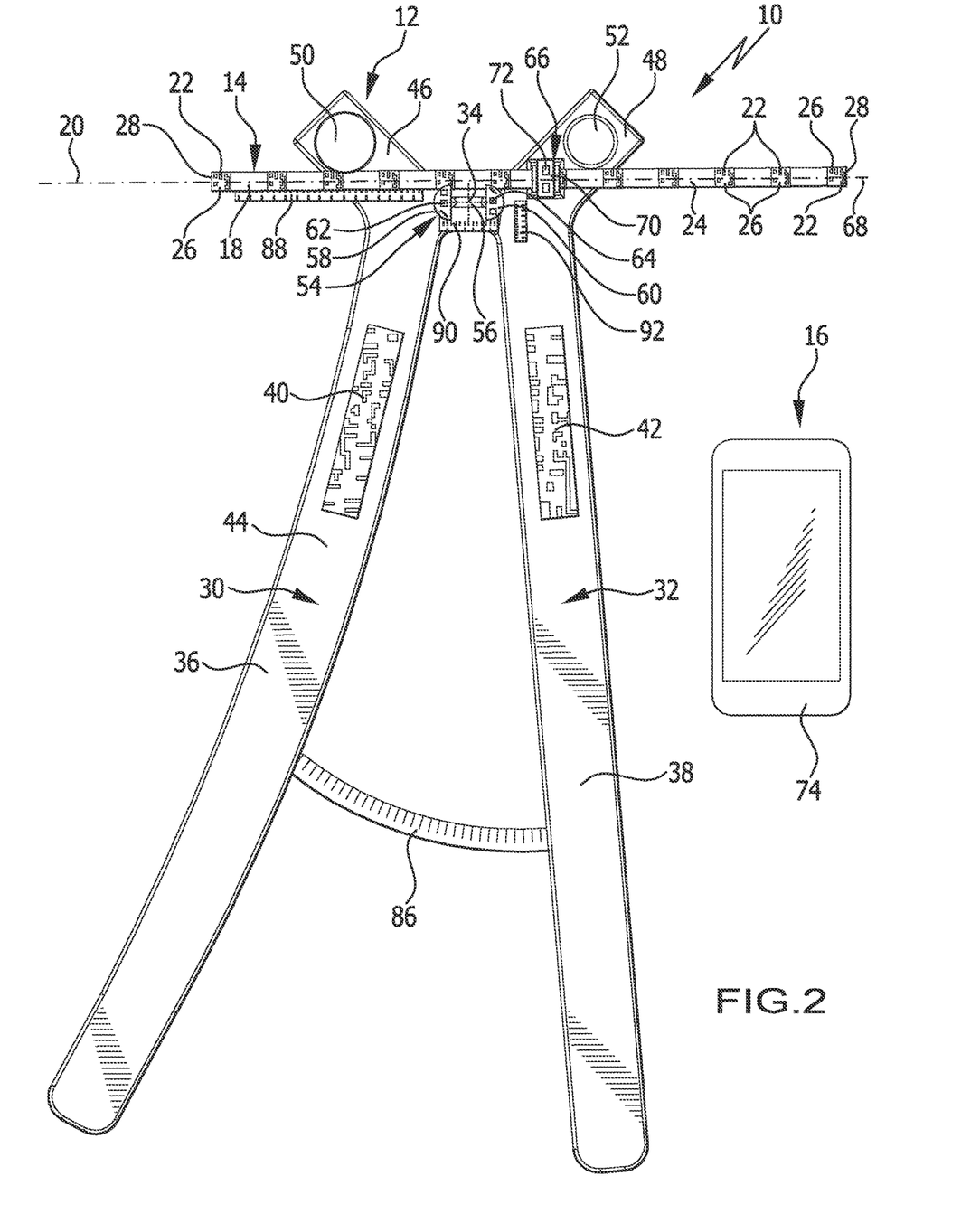
FIG. 2 shows a plan view of the bending system from FIG. 1.

A bending system in accordance with the disclosure, designated in the drawing with the reference numeral 10, comprises a bending apparatus 12, at least one object to be bent 14, and a navigation device 16.

The object to be bent 14 is presently configured as a surgical rod 18 of a surgical fixation system. Here, the rod 18 is used to connect anchoring elements, in particular bone screws, to one another, which elements are not depicted in the drawing. The bone screws are anchored, in particular, to vertebral bodies and are to be fixed relative to one another by means of the rod 18. This requires giving the rod 18 a desired shape by bending. This requires converting the rod 18 from an initial shape into the desired shape by means of the bending apparatus 12. This is effected while setting and considering bending parameters, which comprise the bending position on the rod, the bending angle, the bending radius, and the bending plane.

In the present case, the rod 18 is of elongate configuration and is embodied in cylindrical form. The rod 18 hereby defines an axis 20.

Markings 22 are applied to the rod 18. The markings 22 are arranged on and integrally formed in a surface 24 of the rod 18, for example by means of anodic oxidation, water printing methods or by a material-removing exposure method, in particular by an ultra-short pulse laser (in particular ps-laser). The markings 22 preferably do not or substantially do not project over the surface 24.

The markings on the object to be bent 14 and on the bending apparatus 12 favorably do not impair the respective structure and, in particular, stability thereof, and/or the respective sterilizability thereof is not impaired by the markings.

The markings 22 are configured as peripheral rings 26, which are spaced at a distance from one another in the axial direction 20. The peripheral rings 26 are hereby arranged equidistant from one another. The rod 18 also has markings 22 on respective opposing end sides 28.

Provision may be made that the markings 22 of the rod 18 are identical or differ from one another at least in part.

It is favorable if the markings 22, in particular those on the end sides 28, are designed such that the navigation device 16 can determine when a rotation of the rod 18 about the axis 20 takes place. For example, the peripheral rings are interrupted in the peripheral direction.

In the use of the bending system 10, the rod 18 may be selected from a stock of different or like rods, which will be explained in the following.

In the present case, the bending apparatus 10 is hand-operable and comprises two pivot elements 30, 32, which are mounted on one another so as to be pivotable about a pivot axis 34. For actuation by the user, the pivot elements 30, 32 comprise branches 36 and 38, respectively, which can be grasped by the user with his hand and be pivoted relative to one another with a view to setting the bending angle as a bending parameter.

Markings 40, 42, which presently differ from one another, are arranged on the branches 36, 38. The markings 40, 42 are integrally formed on surfaces 44 of the branches 36, 38 in one of the manners described above with the example of the markings 22. Here, the markings 40, 42 are, for example, of two-dimensional configuration and are formed in the surface itself.

By means of the navigation device 16, it is possible, for one, to detect the bending apparatus 12 by means of at least one of the markings 40, 42. The bending apparatus 12 with the markings 40, 42 thereby forms a reference for defining a reference coordinate system in which the rod 18 can be detected with regard to relative position and relative orientation to the bending apparatus 12.

For another, the navigation device 16 can detect the relative orientation of the markings 40, 42 in dependence on the relative position of the branches 36, 38 during the pivot movement and derive the bending angle herefrom.

The pivot elements 30, 32 each comprise a projection 46, 48. Abutment elements 50 and 52 are arranged on the projections 46, 48, respectively, for placing the rod 18. The abutment elements 50, 52 are spaced at a distance from one another. Upon actuation of the branches 36, 38, the abutment elements 50, 52 pivot in relation to the pivot axis 34.

The bending apparatus 12 comprises a further abutment element 54. The abutment element 54 is presently arranged in the region of a portion 56 of the bending apparatus 12 at which the pivot elements 30, 32 are pivotably mounted on one another and connected to one another. When the rod 18 abuts against the abutment elements 50, 52, and 54, the abutment element 54 abuts against a side of the rod 18 that is opposite the side contacting the abutment elements 50, 52. The rod 18 thus passes between the abutment elements 50, 52 on the one side and the abutment element 54 on the other side.

The abutment element 54 comprises a first abutment member 58 and a second abutment member 60. The abutment members 58, 60 can be brought into different distances from one another (including zero distance), for example by displacement. The further apart the abutment members 58, 60 are spaced from one another, the greater the bending radius becomes to which the rod 18 is bent upon actuating the branches 36, 38.

Markings 62, 64 are arranged on the abutment members 58, 60. Said markings 40, 42 are integrally formed on the surfaces 44 of the abutment members 58, 60 in the manners described above with the example of the markings 22. For example, the markings 62, 64 are differently configured.

The distance of the abutment members 58, 60 from one another can be determined by way of the markings 62, 64 with a view to determining the bending radius as a bending parameter.

Provision may be made that the abutment members 58, 60 are jointly moveable on the bending apparatus 12, in particular transversely to the direction of the change in distance, with a fixed spacing from one another for influencing the bending radius. The relevant position of the abutment members 58, 60 can, e.g., be determined and/or monitored by means of a marking on the bending apparatus 12, for example a reference marking on the bending apparatus 12.

In the present case, the bending apparatus 12 further comprises a rotation receptacle 66. The rotation receptacle 66 comprises a rotation element 70 defining an axis 68. The rod 18 can be passed through the rotation element 70. In this case, the axes 20, 68 coincide. The rotation element 70 is hand-operable, whereby the rod 18 can be rotated about the axis 68. This makes it possible to vary the bending plane in which the bending of the rod 18 takes place.

A marking 72 is arranged on the rotation element 70. The marking 72 is formed, e.g., integrally on the surface of the rotation element 70 in one of the manners described above with the example of the markings 22. Here, the marking 72 is designed such that the navigation device 16 is able to determine which rotation angle the rotation element 70 and thus the rod 18 adopts relative to the bending apparatus 12 or by which rotation angle the rod 18 is rotated.

In the present case, the rotation receptacle 66 is positioned on the projection 48 between the abutment elements 52 and 54, this positioning being nonlimiting.

The navigation device 16 is presently configured as an integrated navigation device, in particular as a smartphone 74.

The navigation device 16 comprises a data processing unit 76, which comprises, e.g., a microprocessor, a detection unit 78, a storage unit 80, and an indication unit 82 with a display unit 84. The latter is, in particular, the touchscreen of the smartphone 74. The detection unit 78 comprises, in particular, the camera of the smartphone 74.

As described, e.g., in EP 2 910 206 A1, it is possible for the user to determine the relative positions of the anchoring elements. In this way, it can be determined how the rod 18 must be shaped so that the anchoring elements can be connected to one another.

For the purposes of the latter, the navigation device 16 may preferably be used. A sensor unit of the navigation device 16, which comprises, e.g., the camera or angle or inertial sensors, serves to detect the positions of the anchoring elements. The desired shape of the rod 18 can be calculated by the data processing unit 76 and then, e.g., stored in the storage unit 80.

Information on a plurality of rods can be stored in the storage unit 80. The data processing unit 76 can make suggestions to the user on the indication unit 82 as to which of the rods should preferably be used for the connection of the anchoring elements and be selected for the bending operation.

A user application program, for example in the form of a so-called "app", is executably stored in the storage unit 80 in order to instruct the user in a handling-friendly and intuitive manner to bend the rod 18.

The bending parameters calculated by the data processing unit 76 can be monitored during the bending operation by the bending apparatus 12 and the rod 18 being tracked on the basis of the markings 22, 40, 42, 62, 64, and 72. This makes it possible, in particular, to determine whether the actual value of a bending parameter has a calculated desired value or deviates therefrom. Moreover, by time-dependently determining the actual values of the bending parameters by means of tracking the markings 22, 40, 42, 62, 64, and 72, in particular, changes in the respective values can be determined. The user can be optically and/or acoustically and/or haptically informed of the development of the value of the bending parameter by way of the indication unit 82.

Provision may be made that the data processing unit 76 considers material properties (for example due to the possible elastic deformation) of the rod 18 in the determination of the bending parameters.

Provision may be made that the user changes at least one parameter on the navigation device 16. For example, the position of bone screws can be varied and the altered shape of the rod 18 is calculated. Alternatively or in addition, provision may be made that the user changes at least one bending parameter.

Figure 3:
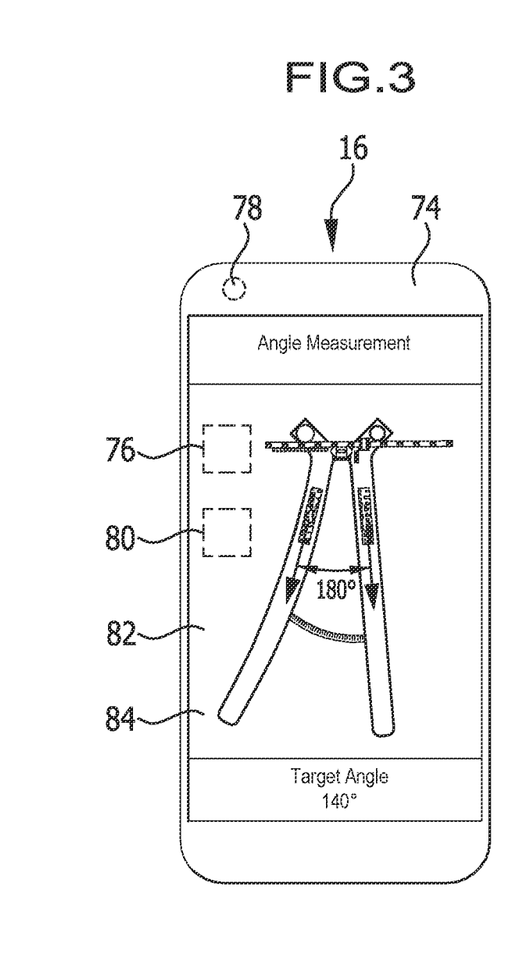
FIG. 3 shows a plan view of a display unit of the navigation device during the bending operation.

FIG. 3 shows as an example the monitoring of the bending parameter "target angle" under the heading "Angle Measurement". For this purpose, the navigation device 16 can detect the markings 40, 42 and evaluate the relative position of the branches 36, 38 on the basis of the detected markings. In the example, the rod 18 is to be bent commencing from the actual value of 180° for the bending angle to a desired value of 140°. The user is instructed to actuate the branches 36, 38.

Figure 4:
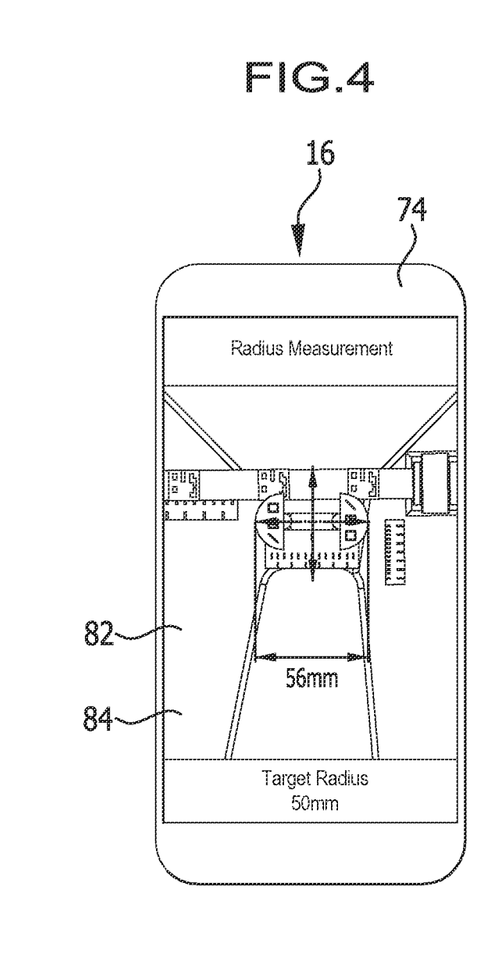
FIGS. 4-7 show further representations corresponding to FIG. 3 during the bending operation.

FIG. 4 shows as an example the monitoring of the bending parameter "bending radius" under the heading "Radius Measurement". Commencing from an initial actual value of the bending radius of 56 mm, the bending radius in the example is to be set to a desired value of 50 mm. The relevant information comes from the evaluation of the detected markings 62, 64.

The user is instructed to vary the distance of the abutment members 58, 60 until the desired value of the bending radius can be achieved.

Figure 6:
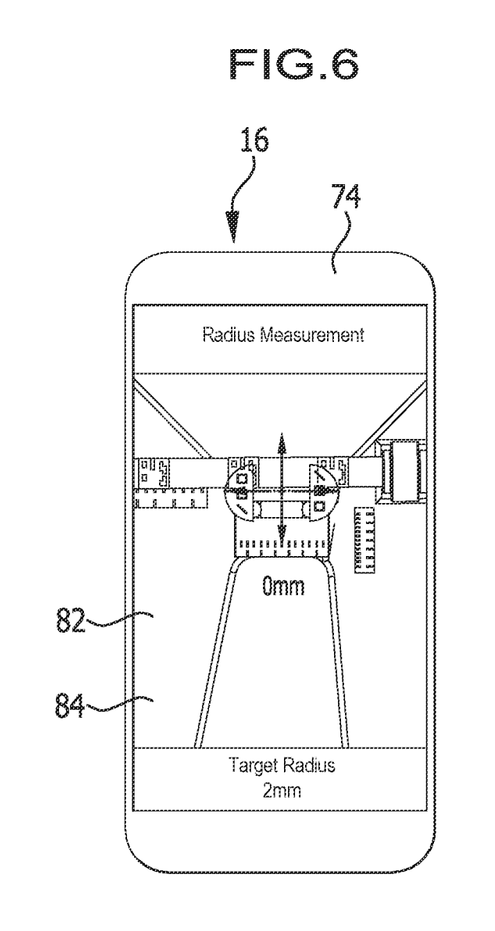

FIG. 6 depicts a similar case for a different actual value and a different desired value of the bending radius. Moreover, the abutment members 58, 60 are displaced together, transversely and, in particular, perpendicularly to the direction of the change in distance.

Figure 5:
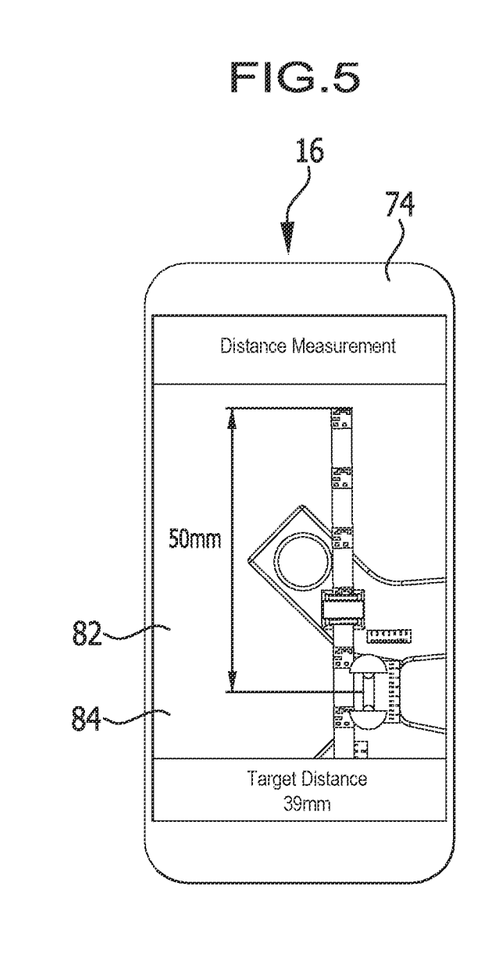

FIG. 5 shows as an example under the heading "Distance Measurement" the monitoring of a bending position as a bending parameter, the rod 18 being bent at the bending position.

For this purpose, the navigation device 16 can use the position of the rod 18 relative to the bending apparatus 12 on the basis of the detected markings 22, 62, and 64. For example, the distance of an end side 28 from the abutment members 58, 60 is determined and from this the position on the rod 18 at which the bending operating takes place is determined. The actual value for the bending position of 50 mm indicates to the user to displace the rod 18 relative to the bending apparatus 12 in such a way that the desired value of 39 mm for the bending position is achieved.

Figure 7:
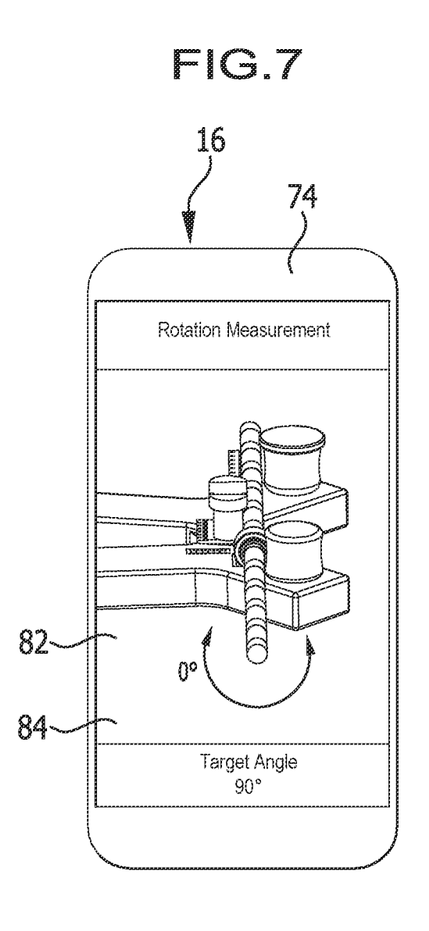

FIG. 7 shows under the heading "Rotation Measurement" the monitoring of the bending plane about which the rod 18 is bent. The navigation device 16 can thereby calculate the rotation angle of the rotation element 70 on the bending apparatus 12 on the basis of the detected marking 72, and preferably the marking 22.

In the present case, the user is advised that the rod 18 is to be rotated by means of the rotation element 70 until the actual value for the bending plane as a bending parameter has been changed from 0° to the desired value of 90°.

The user is, in particular, guided by the application program on the basis of a defined plan of procedure, for example a workflow, to ensure that at the end of the bending operation all bending parameters have been correctly followed and that the rod 18 has the desired shape.

The views in FIGS. 3 to 8 may be real depictions of the bending apparatus 12 and the rod 18 that are created using the camera, and/or may be exemplary, non-real depictions. The linking of exemplary depictions and real depictions and/or indications to augmented reality depictions is possible.

Figure 8:
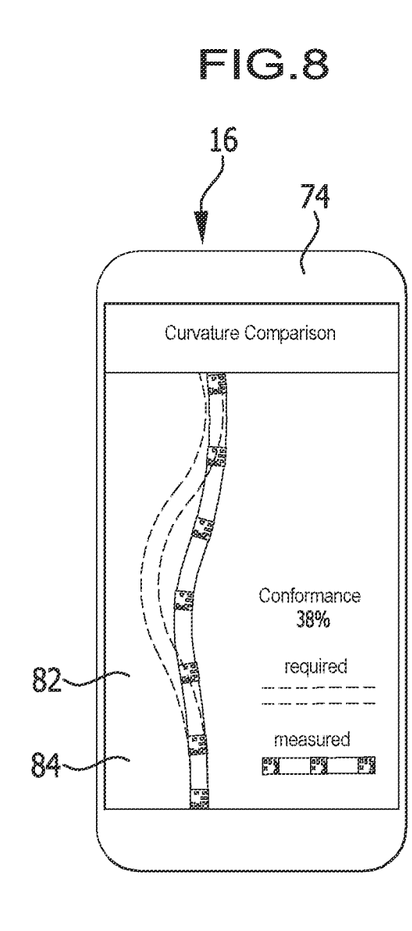
FIG. 8 shows a plan view of the navigation device on the display unit of which an actual shape is depicted for comparison with the desired shape of the object to be bent.

FIG. 8 depicts as an example under the heading "Curvature Comparison" how the navigation device 16 performs a comparison of the actual shape of the rod 18 that is determined on the basis of the markings 22 with the desired shape of the rod 18.

The determined actual shape (solid lines with the images of the marking 22) is thereby compared with the desired shape (dashed lines) on the display unit 84. It is immediately apparent to the user that the rod 18 has not been properly deformed and that further bending operations are necessary.

The bending apparatus 12 further comprises display elements 86, 88, 90, and 92. Using the display elements 86, 88, 90, and 92, which, in particular, comprise scales, the user can read off and determine values for the bending parameters.

The display element 86 allows the user to determine the angular position of the branches 36, 38 relative to one another in order to determine the bending angle.

The display element 88 allows the user to determine the relative position of the rod 18 to the abutment element 54 in order to determine the bending position as a bending parameter.

The display element 90 allows the user to determine the relative position of the abutment members 58, 60 to one another in order to determine the bending radius as a bending parameter. Provision may further be made that by means of the display element 90 or a separate display element, the position of the abutment members 58, 60 can be determined when displaced together transversely to the direction of the change in distance.

The display element 92 allows the user to determine the rotational position of the rotation element 70 in order to determine the bending plane as a bending parameter.

What is claimed:

1. A medical bending system comprising:
   an object to be bent;
   a bending apparatus with which the object to be bent is bendable; and
   a navigation device with a detection unit and a data processing unit,
   the object to be bent comprising first markings arranged or formed on a surface of the object to be bent, and the bending apparatus comprising second markings that are arranged or formed on the bending apparatus,
   said first and second markings being optically detectable by the detection unit,
   the data processing unit being configured to determine at least one bending parameter during a bending operation based on information from the detection unit relating to the first and second markings,
   wherein at least one of the following applies:

the first markings are integrated into or formed on said surface of the object to be bent by anodic oxidation, a shape-changing exposure method or water print coating; and the second markings are integrated into or formed on said surface of the bending apparatus by anodic oxidation, a shape-changing exposure method or water print coating.

2. The medical bending system according to claim 1, wherein the navigation device is or comprises an integrated navigation device that comprises the detection unit, the data processing unit, and an indication unit.

3. The medical bending system according to claim 2, wherein the navigation device is or comprises a smartphone, a tablet computer, or a head mounted device (HMD).

4. The medical bending system according to claim 1, wherein a desired shape of the object to be bent is determinable by the data processing unit based on data from a sensor unit of the navigation device to connect a plurality of connecting elements, arranged in a defined relative arrangement, by way of the object to be bent.

5. The medical bending system according to claim 1, wherein a predeterminable desired shape of the object to be bent is stored in a storage unit of the navigation device, and wherein indications to a user regarding at least one of the following are outputted on an indication unit of the navigation device:
  indications for operating the bending apparatus, wherein an actual value of the at least one bending parameter is determined and an actual shape of the object to be bent is determined based on said actual value of the at least one bending parameter and is compared with the desired shape;
  indications when an actual value of the at least one bending parameter has a desired value or differs therefrom; and
  indications relating to selection of a selected object to be bent from a set of available objects to be bent.

6. The medical bending system according to claim 5, wherein the first markings and the second markings are detected by the detection unit during the bending operation and indications to the user are provided by the data processing unit relating to the actual shape of the object to be bent.

7. The medical bending system according to claim 1, wherein the first markings comprise peripheral rings arranged on the object to be bent and spaced at a distance from one another in a longitudinal direction of the object to be bent.

8. The medical bending system according to claim 1, wherein the second markings comprise at least one of the following:
  flatly extended markings on surfaces of branches of the bending apparatus;
  at least one marking on a rotation receptacle with which the object to be bent is held on the bending apparatus so as to be rotatable about an axis; and
  at least one marking on an abutment element for placing the object to be bent during the bending operation.

9. The medical bending system according to claim 1, wherein the data processing unit uses at least one of the second markings for defining a reference coordinate system in space in which a position of the object to be bent relative to the bending apparatus is determinable.

10. The medical bending system according to claim 1, wherein the data processing unit, based on detection of the first markings and the second markings, determines at least one of:
  a relative position of the object to be bent and the bending apparatus; and
  a position of the object to be bent on at least one abutment element of the bending apparatus with regard to a bending position as the at least one bending parameter.

11. The medical bending system according to claim 1, wherein at least one of the following applies:
  the data processing unit determines an orientation of the object to be bent relative to the bending apparatus based on a marking of a rotation receptacle of the bending apparatus with regard to a bending plane as the at least one bending parameter; and
  the data processing unit determines an actual shape of the object to be bent.

12. The medical bending system according to claim 11, wherein the data processing unit determines the actual shape of the object to be bent for comparison with a desired shape of the object to be bent, based on the first markings.

13. The medical bending system according to claim 1, wherein the bending apparatus comprises abutment elements for the object to be bent, which are positioned at a distance from one another and are pivotable relative to one another, wherein the abutment elements are arranged or formed on pivot elements that are pivotable in relation to one another, wherein the second markings are on the pivot elements, and wherein the data processing unit determines a bending angle as the at least one bending parameter based on the second markings.

14. The medical bending system according to claim 13, wherein the bending apparatus comprises a delimiting element with which a range of the pivoting of the pivot elements relative to one another is delimitable, and wherein an indication to a user for setting the delimiting element is providable on an indication unit to achieve a predetermined bending angle when the pivot elements are pivoted until the delimiting element comes into effect.

15. The medical bending system according to claim 1, wherein the bending apparatus is hand-operable.

16. A medical bending system comprising:
  an object to be bent;
  a bending apparatus with which the object to be bent is bendable; and
  a navigation device with a detection unit and a data processing unit,
  the object to be bent comprising first markings arranged or formed on a surface of the object to be bent, and the bending apparatus comprising second markings that are arranged or formed on the bending apparatus,
  said first and second markings being optically detectable by the detection unit,
  the data processing unit being configured to determine at least one bending parameter during a bending operation based on information from the detection unit relating to the first and second markings,
  wherein the first markings comprise peripheral rings arranged on the object to be bent and spaced at a distance from one another in a longitudinal direction of the object to be bent.

17. The medical bending system according to claim 16, wherein the bending apparatus comprises abutment elements for the object to be bent, which are positioned at a distance from one another and are pivotable relative to one another, wherein the abutment elements are arranged or formed on pivot elements that are pivotable in relation to one another, wherein the second markings are on the pivot elements, and wherein the data processing unit determines a bending angle as the at least one bending parameter based on the second markings.

18. A medical bending system comprising:
an object to be bent;
a bending apparatus with which the object to be bent is bendable; and
a navigation device with a detection unit and a data processing unit,
the object to be bent comprising first markings arranged or formed on a surface of the object to be bent, and the bending apparatus comprising second markings that are arranged or formed on the bending apparatus,
said first and second markings being optically detectable by the detection unit,
the data processing unit being configured to determine at least one bending parameter during a bending operation based on information from the detection unit relating to the first and second markings,
wherein the second markings comprise at least one of:
flatly extended markings on surfaces of branches of the bending apparatus;
at least one marking on a rotation receptacle with which the object to be bent is held on the bending apparatus so as to be rotatable about an axis; and
at least one marking on an abutment element for placing the object to be bent during the bending operation.

19. The medical bending system according to claim 18, wherein the bending apparatus comprises abutment elements for the object to be bent, which are positioned at a distance from one another and are pivotable relative to one another, wherein the abutment elements are arranged or formed on pivot elements that are pivotable in relation to one another, wherein the second markings are on the pivot elements, and wherein the data processing unit determines a bending angle as the at least one bending parameter based on the second markings.

20. A medical bending system comprising:
an object to be bent;
a bending apparatus with which the object to be bent is bendable; and
a navigation device with a detection unit and a data processing unit,
the object to be bent comprising first markings arranged or formed on a surface of the object to be bent, and the bending apparatus comprising second markings that are arranged or formed on the bending apparatus,
said first and second markings being optically detectable by the detection unit,
the data processing unit being configured to determine at least one bending parameter during a bending operation based on information from the detection unit relating to the first and second markings,
wherein the bending apparatus comprises abutment elements for the object to be bent, which are positioned at a distance from one another and are pivotable relative to one another, wherein the abutment elements are arranged or formed on pivot elements comprising branches that are pivotally mounted on one another, wherein the second markings are on the pivot elements, and wherein the data processing unit determines a bending angle as the at least one bending parameter based on the second markings, and
wherein the bending apparatus comprises a delimiting element with which a range of the pivoting of the pivot elements relative to one another is delimitable, and wherein an indication to a user for setting the delimiting element is providable on an indication unit to achieve a predetermined bending angle when the pivot elements are pivoted until the delimiting element comes into effect.

21. The medical bending system according to claim 20, wherein the bending apparatus comprises abutment elements for the object to be bent, which are positioned at a distance from one another and are pivotable relative to one another, wherein the abutment elements are arranged or formed on pivot elements that are pivotable in relation to one another, wherein the second markings are on the pivot elements, and wherein the data processing unit determines a bending angle as the at least one bending parameter based on the second markings.

* * * * *